United States Patent [19]

Houghten

[11] Patent Number: 4,631,211

[45] Date of Patent: Dec. 23, 1986

[54] MEANS FOR SEQUENTIAL SOLID PHASE ORGANIC SYNTHESIS AND METHODS USING THE SAME

[75] Inventor: Richard A. Houghten, Solana Beach, Calif.

[73] Assignee: Scripps Clinic & Research Foundation, La Jolla, Calif.

[21] Appl. No.: 715,654

[22] Filed: Mar. 25, 1985

[51] Int. Cl.[4] .................... D03D 1/04; B65D 33/01; C08F 283/00

[52] U.S. Cl. ...................................... 428/35; 139/389; 383/102; 525/54.11

[58] Field of Search .................... 139/389; 428/35; 383/102; 525/54.11

[56] References Cited

U.S. PATENT DOCUMENTS

| | | | |
|---|---|---|---|
| 3,544,404 | 12/1970 | Johnson et al. | 139/389 |
| 4,226,857 | 11/1980 | Momany | 525/54.11 |
| 4,282,143 | 8/1981 | Sarantakis | 525/54.11 |
| 4,304,692 | 12/1981 | Hughes et al. | 525/54.11 |
| 4,483,964 | 11/1984 | Urdea et al. | 525/54.11 |
| 4,507,433 | 3/1985 | Miller et al. | 525/54.11 |

OTHER PUBLICATIONS

Merrifield, *Solid Phase Peptide Synthesis*, Journal American Chemical Society, vol. 85, pp. 2149–2154, 1963.

*Primary Examiner*—John E. Kittle
*Assistant Examiner*—James J. Seidleck
*Attorney, Agent, or Firm*—Dressler, Goldsmith, Shore, Sutker, & Milnamow, Ltd.

[57] ABSTRACT

A means for carrying out sequential, solid phase syntheses is disclosed as are methods of its use. The synthesis means comprises a foraminous container that encloses reactive particles. The particles are larger than any of the foraminae and have a known amount of covalently linked organic synthesis reactive functionality that is capable of reacting during the organic syntheses. The container and particles are substantially insoluble in water.

40 Claims, 10 Drawing Figures

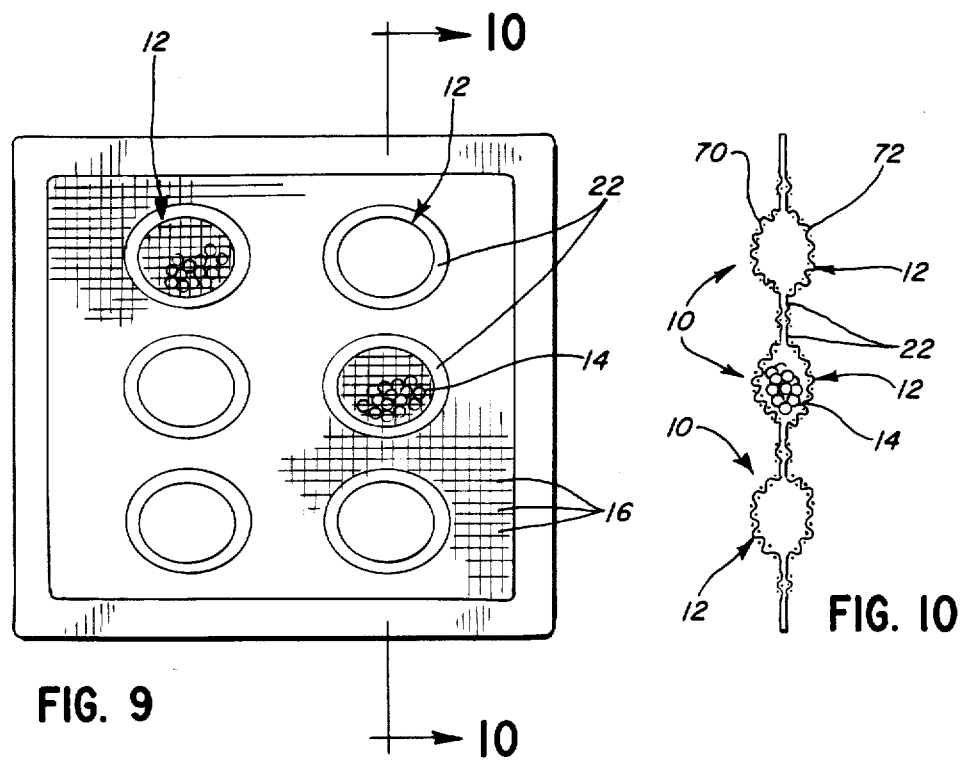

MEANS FOR SEQUENTIAL SOLID PHASE ORGANIC SYNTHESIS AND METHODS USING THE SAME

DESCRIPTION

1. Technical Field

The present invention relates to organic synthesis, and more specifically to those syntheses that are carried out on a solid phase support and in which a plurality of chemically similar subunits are coupled to the solid phase to form a sequence of subunits.

2. Background Art

In the last several years there has been an escalating need for synthetic polypeptides in a wide variety of applications. Exemplary of such applications are the detailed study of antigen-antibody interactions, the development of synthetic polypeptide vaccines, the optimization of polypeptide antigens of clinical diagnostic utility, the mapping of brain-specific genes, and the study of protein conformational parameters. In the majority of such applications to date, a limiting factor has been the availability and cost of the desired polypeptides. Clearly, such applications would be greatly facilitated if larger numbers of polypeptides could be synthesized more rapidly and at a lesser cost than as heretofore been possible.

In particular, the recent finding that antibodies raised against peptides frequently react with sites in a protein has opened the way for a site-specific immunological methodology of unprecedented precision. Sutcliffe et al., *Nature (London)*, 287, 801-805 (1980); Lerner, *Nature (London)*, 299, 592-596 (1982); Green et al., *Cell*, 23, 477-487 (1982); Bittle et al., *Nature (London)*, 298, 30-33 (1982). Thus, instead of defining the reactivity of a given antibody at the protein or subunit level, the binding can be described in terms of a short sequence of amino acid residues of clearly defined length. Wilson et al., *Cell*, 37, 767-778 (1984); Niman et al., *Proc. Natl. Acad. Sci. USA*, 80, 4949-4953 (1983). Clearly, the next advance, is to refine the understanding of the antigenic sites in proteins at the level of individual amino acid residues. This challenge, however, requires the synthesis of a large number of distinct polypeptides.

While the art has progressed since the first solid phase syntheses were disclosed, the preparation of hundreds of 10 to 20 milligram (mg) quantities of polypeptides containing about 10 to about 20 amino acid residues per polypeptide in a span of one month has not been possible without a tremendous capital outlay for the purchase of many polypeptide synthesizing machines and the human experts to run such machines.

The pioneering work of R. B. Merrifield and coworkers from 1963 [*J. Am. Chem. Soc.*, 85, 2149-2154] has made possible the synthesis of polypeptides that could not be otherwise synthetically prepared. In addition, those polypeptides that could be prepared by previous techniques could, after Merrifield's disclosures, be prepared far more readily.

Merrifield's synthesis of polypeptides by solid phase methodology is almost universally still used today. That method utilizes a reservoir containing a polymeric solid support linked to the carboxyl-terminal amino acid residue of the desired polypeptide by a selectively severable, labile covalent bond. The alpha amine group of that residue is protected by a selectively removable blocking (protecting) group. The addition of further amino acid residues is a process that uses repetitive wash, deprotection, neutralization and coupling steps.

In usual syntheses, only a single amino acid residue-containing resin at a given time is used in the synthesis of a polypeptide. Methods have been presented that utilize two differently sized resins enabling one to carry out two syntheses simultaneously, thus preparing two analogues at a given time [van Rietschoten et al., in *Peptides* 1974, Y. Wolman ed., Wiley and Sons, New York, 113-116 (1975)]. Additionally, as many as four syntheses at a given time have been reported using a specific apparatus Gorman, *Anal. Biochem.*, 136, 397-406 (1984). However, both of those methods are limited in scope and practicality.

An interesting methodology involving the synthesis of polypeptides permanently bound to a solid support and the interaction of those solid support bound polypeptides with antisera has recently been presented Geysen et al., *Proc. Natl. Acad. Sci. USA*, 81, 3998-4002 (1984); Geysen et al., *Proc. Natl. Acad. Sci. USA*, 82, 178-182 (1985). However, that procedure suffers in that only microgram amounts of polypeptide can be generated, and those polypeptides are not removable from the solid support. Also, the effect of the solid support on the interaction of the antibody with the polypeptides is unclear.

If one desired significant amounts (e.g., 10-20 mg or greater) of polypeptide analogs containing a variety of single amino acid substitutions at a given point, or polypeptides shortened at the carboxyl-terminus in the polypeptide chain, until now, a separate synthesis for each of those polypeptides was required. This is true even though all of the deprotecting, washing, neutralization, and coupling steps for each polypeptide are identical except at the position varied.

Shortly after the breakthrough of Merrifield as to the synthesis of polypeptides, R. L. Letsinger and his co-workers developed solid phase synthetic techniques for preparing oligonucleotides. See for example, Letsinger and Mahadevan, *J. Am. Chem. Soc.*, 87, 3526 (1965). The techniques pioneered by Letsinger et al. have helped to spawn new commercial ventures in the area of machines for automated syntheses of oligo- and polynucleotides, and have aided in the current wave of genetic engineering. Nevertheless, the synthesis of large numbers of such nucleotides in a relatively short time is still limited by capital outlays for machines and the technical expertise to run them.

It would therefore be beneficial if a means could be found to expedite the preparation of multi-milligram quantities of large numbers of synthetically produced organic reaction product molecules such as polypeptides and oligo- or polynucleotides.

BRIEF SUMMARY OF THE INVENTION

The present invention contemplates a means for carrying out a sequential solid phase organic synthesis to form a reaction product molecule that contains a plurality of reacted subunits. In one embodiment, that means comprises a foraminous container that encloses a known quantity of reactive particles. Each of those reactive particles is of a size that is larger than any of the foraminae. The particles contain a known amount of covalently linked organic synthesis reactive functionality that is capable of reacting during the organic synthesis being performed. The container and the particles are substantially insoluble in water and in organic solvents, do not react with any chemicals used in the synthesis, and in particularly preferred practice are non-reactive with hydrogen fluoride.

In another aspect, a particularly preferred synthesis means contains a known quantity of solid support particles, which are preferably hydrophobic, solid phase resin beads, enclosed therein. Those particles have a known amount of identical organic synthesis subunits covalently linked to the particles by selectively severable covalent bonds. In addition, each of the subunits contains a functional group that is capable of reacting during the organic synthesis but is protected from so reacting by a selectively removable, covalently linked protecting group. Particularly preferred subunits are selected from the group consisting of (i) an alpha amino group-protected amino acid residue and (ii) an alpha amino group-protected and reactive side chain protected amino acid residue.

Methods of carrying out sequential, solid phase organic syntheses to form a reaction product containing a plurality of desired reacted subunits of a predetermined sequence are also contemplated.

One of those methods contemplates the following steps:

(a) A before-described means for carrying out sequential solid phase organic synthesis is provided. That means includes a foraminous container that encloses reactive particles that contain a reactive functionality.

(b) First subunits are reacted with the reactive functionalities to form a selectively severable covalent bond between the first subunits and the particles to thereby form a synthesis means containing particle-linked subunits. The first subunits include a first functional group that reacts with the reactive functionality of the particles and a second reactive functional group that is capable of reacting during the organic synthesis, but that is protected from reaction by a selectively removable, covalently linked protecting group.

(c) The protecting groups of the second reactive functional groups are removed to form a synthesis means containing particle-linked subunits having free reactive functional groups.

(d) The synthesis means containing particle-linked subunits having free reactive functional groups is admixed with an excess of identical, known other subunits that contain (i) a functional group capable of reacting with the free reactive groups of the particle-linked subunits, and (ii) a second reactive functional group such as an alpha amine of an amino acid or a 5'-hydroxyl of a nucleoside that is capable of reacting during the organic synthesis, but is protected from so reacting by being covalently linked to a selectively removable protecting group.

(e) The free reactive groups and the admixed functional groups are reacted to form covalent bonds, couple the subunit to the particle and thereby form particle-linked reaction products.

(f) Unreacted subunits are separated from the particle-linked reaction products.

(g) The protecting groups of the coupled subunits of step (d) are removed to form particle-linked reaction products containing free reactive functional groups.

(h) Thereafter, steps (d), (e), (f) and (g) are serially repeated until particle-linked reaction products containing the desired number and identity of reacted subunits are synthesized.

(i) The selectively severable bond between the first-named subunits and the particles are severed to form a mixture of severed, free reaction products and reacted particles.

(j) The severed, free reaction products are separated from the reacted particles.

(k) The separated, free reaction products are then recovered.

Another aspect of the methods contemplates the steps of:

(a) Providing a before-described foraminous container means for carrying out sequential solid phase organic synthesis that encloses particles having selectively severable, covalently linked subunits that include a selectively removable protecting group covalently bonded to a subunit reactive functional group.

(b) The protecting groups are removed to form a synthesis means containing resin-linked subunits having a free reactive groups.

(c) An excess of identical other subunits that contain (i) a second reactive functional group capable of reacting with the free reactive groups of the resin-linked subunits, and (ii) another reactive functional group that is capable of reacting during the organic synthesis, but that is protected from so reacting by a selectively removable, covalently bonded protecting group is admixed with the synthesis means.

(d) The free reactive groups and the second reactive groups are reacted to form covalent bonds, couple the admixed subunit to the resin and thereby form resin-linked reaction products.

(e) Unreacted other subunits are separated from the resin-linked reaction products.

(f) The protecting groups of step (c) are selectively removed to form resin-linked reaction products containing free reactive functional groups.

(g) Thereafter, steps (c), (d), (e) and (f) are serially repeated until resin-linked reaction products containing the desired number and identity of reacted subunits are synthesized.

(h) The selectively severable bonds between the first-named subunits and the resin are severed to form severed, free reaction products and reacted particles.

(i) The severed, free reaction products are separated from the reacted particles.

(j) The free severed reaction products are then recovered.

Another aspect of this invention is a method for simultaneously covelently bonding a subunit to each of a plurality of particle-linked subunits without intermingling subunit. This method comprises the steps of:

(a) Providing an admixture containing a plurality of synthesis means each of which comprises a foraminous container having enclosed therein a known quantity of particles, each of the particles being of a size that is larger than any of the foraminae. The particles within the synthesis means have a known amount of organic synthesis subunits covalently linked to the particles by selectively severable bonds. Each such subunit that is farthest from (distal to) the particle/subunit link contains a reactive functional group capable of reacting during the organic synthesis but that is protected from so reacting by a selectively removable, covalently linked protecting group. The containers and particles are substantially insoluble in water and inorganic solvents. In some embodiments, at least one of the plurality of synthesis means containers encloses covalently linked subunits that are of a different chemical identity from the subunits enclosed by another of the synthesis means.

(b) The protecting groups of the particle-linked subunits in each of the synthesis means are selectively removed to form an admixture containing a plurality of synthesis means enclosing particle-linked subunits having free reactive groups.

(c) The admixture of synthesis means so formed is admixed with an excess of identical subunits each of which contains (i) a second reactive functional group capable of reacting with the free reactive group of the particle-linked subunits and (ii) reactive functional groups preferably identical to the free reactive groups of step (b) that are capable of reacting during the organic synthesis, but are protected from so reacting by selectively removable protecting groups.

(d) Covalent bonds between the free reactive groups and the second reactive groups are formed to form an admixture of a plurality of synthesis means enclosing particle-linked subunit reaction products whose last bonded (distal) subunits contain selectively removable, protected reactive functional groups.

(e) The admixed, unreacted subunits are separated from the particle-linked reaction products of the admixture of synthesis means.

(f) Thereafter, the synthesis means are separated from each other.

The present invention provides several benefits and advantages.

One salient benefit is that using the synthesis means and methods described herein, it is now possible to prepare hundreds of related polypeptides in a period of one month or less without large capital outlays for numbers of polypeptide synthesis machines and persons to run them.

A particular advantage of this invention is that several particle-linked subunit sequences that require the addition of one or more of the same subunits may be reacted together without inseparable intermingling of the particle-linked subunit sequences.

Another benefit of the present invention is that 10-20 milligram quantities of each of hundreds subunit sequences may be routinely prepared in a one-month period of time or less at a minimum of expense.

Still further benefits of this invention will be apparent to those skilled in the art from the detailed description that follows:

BRIEF DESCRIPTION OF THE DRAWINGS

In the Figures forming a part of this disclosure, and in which like numerals refer to like structures.

Each of the thirteen bar graphs has a horizontal line on the ordinate that represents 100 percent binding of the monoclonal antibody to the natural sequence. The capital letters below each graph are the single letter code for each residue position in the sequence. Each vertical line in each graph represents the binding of the monoclonal antibody to a polypeptide antigen prepared with the amino acid residue noted below the graph replaced by another amino acid residue; the order of replacing amino acid residues in each graph being in the order of decreasing hydrophobicity, from left to right in each graph, and using the single letter amino acid code: W, F, L, I, Y, V, C, M, P, A, E, G, R, H, D, T, K, Q, S, N.

Figure 6:
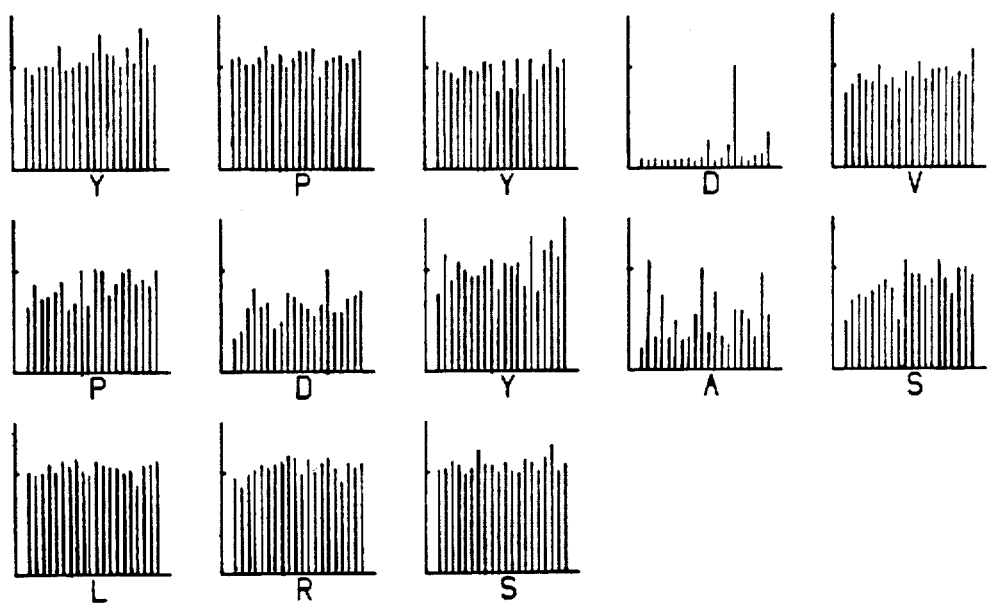
FIG. 6 shows thirteen bar graphs whose individual bars illustrate the relative binding interactions of a single monoclonal antibody raised to a polypeptide corresponding to residues 75-110 from the amino-terminus of the hemagglutinin molecule (HA1) of influenza virus with individual polypeptides prepared in accordance with this invention. Each of the prepared polypeptides corresponded in sequence to the sequence of residue positions 98-110 of the HA1 molecule in which each sequence residue was separately replaced with each of the remaining nineteen naturally occurring amino acids. The 98-110 amino acid residue sequence, written from left to right, in the direction from amino-terminus to carboxy-terminus, and using the single letter amino acid code is: YDYDVPDYASLRS.
Figure 7:
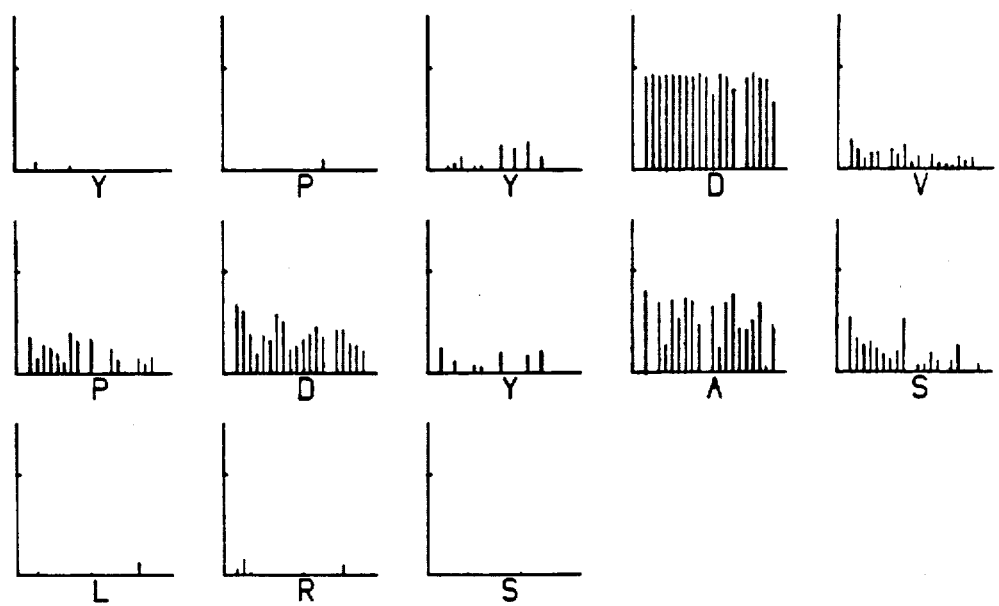

FIG. 7 shows thirteen bar graphs whose individual bars illustrate the decrease in binding of the monoclonal antibody of FIG. 6 to the polypeptides of FIG. 6. Each of the graphs is otherwise as described for FIG. 6.

Figure 8:
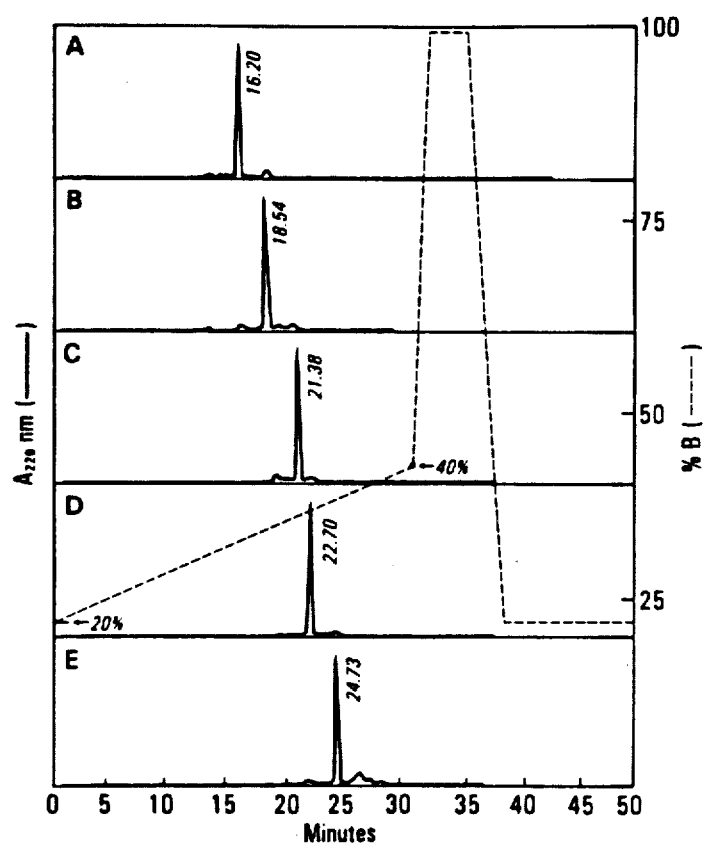

FIG. 8 shows a series of high pressure liquid chromatograph analyses of polypeptide analogues of position 98-110 of the influenza virus hemagglutinin molecule HA1 as described for FIG. 6. The polypeptides analyzed differed at position 100 in containing an arginine (R;part A), threonine (T;part B), tyrosine (Y;part C), or phenylalanine (F;part D) residue. The polypeptides were analyzed in crude form directly following their severance from the particles, extraction and lyophilization. The ordinates are shown in relative units of absorption at 220 nanometers (nm), while the abscissas show relative retention times on the column. The concentration of eluting buffer (% B) is shown with a broken line (- - - - -).

FIG. 9 is an enlarged view of a further embodiment of the present invention comprising a plurality of integrally formed synthesis means of the present invention each of which comprises foraminous container means.

FIG. 10 is a cross-sectional view of the embodiment of the present invention shown in FIG. 9 taken along line 10—10 in FIG. 9.

DETAILED DESCRIPTION OF THE INVENTION

I. General Discussion

The present invention contemplates a means for carrying out a solid phase organic synthesis to form a reaction product molecule containing a plurality of reacted subunits present in a known sequence of subunits. Solid phase organic synthesis is the preparation of organic molecules such as polypeptides and oligo- or polynucleotides on a solid phase support such as particles of resin, glass or glass-resin composites. The organic molecules such as polypeptides and oligonucleotides prepared by such techniques as utilized in this invention contain two or more subunits such as amino acid or nucleotide residues reacted together by peptide or phosphate bonds, respectively, to form a covalently linked sequence of subunits in which the sequence is known from the reaction conditions employed; i.e., the order in which subunits of known identity were reacted.

The full names for individual amino acid residues are sometimes used herein as are the well-known three-letter abbreviations. The one-letter symbols for amino acid residues are used most often. The Table of Correspondence, below, provides the full name as well as the abbreviation and symbols for each amino acid residue named herein.

| Table of Correspondence | | |
|---|---|---|
| Amino acid | Three-letter abbreviation | One-letter symbol |
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamic acid | Glu | E |
| Glutamine or glutamic acid | Glx | Z |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

A. Containers

Each synthesis means, shown generally in the Figures by the numeral 10, is comprised of a foraminous container 12 that encloses a known quantity of solid phase synthesis particles 14.

The container does not chemically react with and is substantially insoluble in water, acids such as 6 normal sulfuric acid and anhydrous hydrogen fluoride, bases such as 10 normal sodium hydroxide, and organic solvents such as acetone, benzene, toluene, xylene, ethyl acetate, dimethyl sulfoxide, methylene chloride, chloroform, dimethyl acetamide, N-methyl pyrrolidone, dimethyl formamide and the like. Thus, the container is substantially inert to reaction or dissolution with common laboratory liquids. Suitable containers are preferably prepared from polymerized ethylene, propylene and mixtures thereof. Stainless steel and polytetrafluoroethylene may also be utilized as the containers.

Each container 12 includes a sufficient number of foraminae or openings 16 to permit ready entrance and exit of solvent and solute molecules at the reaction temperature, which is typically that of the ambient air of a laboratory. Preferably, the container is prepared from a woven polypropylene mesh, and the foraminae 16 are the interstices between the woven fibers. However, it will be understood that other suitably inactive perforate or porous materials can be readily employed, such as a perforated sheet or a non-woven fabric sheet material.

The foraminae 16 are of a size that is smaller than any of the enclosed reactive particles 14. Thus, the particles 14 are of a size that is larger than any of the foraminae. Exemplary polypropylene mesh is available having interstices of about 35 to about 100 microns.

Stated differently, the mesh foraminae 16 are of a size to retain particles 14 that are retained on a 140 to a 400 standard sieve mesh. More preferably, particles 14 are retained within the foraminae that are retained on a 200 to 400 standard sieve mesh. The foraminae 16 are large enough to permit draining of all solvents used during a solid phase synthesis within a time period of about five minutes, and more preferably, within a time period of about three minutes, the draining times being measured at the temperature of the organic reaction. While containers 12 shown in FIGS. 1-4 are each illustrated as being substantially completely foraminous (i.e., each being formed substantially entirely from mesh materials) it is to be understood synthesis means embodying the principles disclosed herein can be partially foraminous if desired.

The containers 12 enclose the reactive particles 14 and to do so are sealed by a closure means after a quantity of such particles is placed therewithin. Several types of closure means are contemplated, including stitching 20 (see embodiment of FIG. 1), weaving or stapling the container closed with a material that is as substantially inert to the reaction conditions employed as is the container itself. Exemplary of such materials are filaments of polymerized ethylene, propylene, ethylene-co-propylene polymers and stainless steel. Most preferably, however, containers such as those made from polypropylene mesh are heat-sealed closed, and the closure means is thus a substantially continuous heat-seal, such as shown at 18, 20 and 22 in the embodiment of FIGS. 3 and 4.

The containers also preferably include a means for identification 30. The identification means may be a portion of the container such as a flattened, heat-sealed surface at 22 (FIG. 3) that extends from or is a portion of the container. A tab 30 capable of bearing indicia that may be integral to the synthesis means or may be separately affixed to a container by a means such as heat-sealing or a filament 36 that is substantially inert to the reaction conditions, as described hereinbefore, may also be used. The containers 12 may also be identified by cuts or notches 38 placed in a heat sealed edge.

A plurality of synthesis means 10 may also be integrally formed with each other from preferably heat-sealable sheets 70 and 72, at least one of which is foraminous, as is shown in FIGS. 9 and 10. Each of the synthesis means so formed may be the same size, smaller or larger than the previously described individual synthesis means, and contain particles 14 similar to those already described.

In preferred practice the sheets 70 and 72 utilized to form the plurality of synthesis means are formed from polypylene, polyethylene or a polyethylene-polypropylene copolymer mesh, and are heat-sealed at 22 to form the integral plurality of individual synthesis means containers 12. A suitable surface capable of bearing indicia may be formed by heat sealing the peripheral edges of the foraminous sheets 70 and 72. The mesh of the sheets 70 and 72 provides the foraminae 16 for the containers 12.

B. Enclosed Particles

A container of a synthesis means of this invention encloses a known quantity of solid phase synthesis particles 14. The particles 14 may be comprised of one or more constituents and include a covalently linked reactive functionality or a subunit covalently linked to the particle by a selectively severable bond.

The particles are also referred to in the art as solid supports. The phrases "particle" and "solid support" and their plurals are used interchangeably herein.

1. Particles with Reactive Functionalities

Several solid supports containing covalently linked reactive functionalities have been described in the chemical and biochemical literature, and any such support may be utilized so long as the solid support is insoluble in water, in the before-mentioned organic solvents and is substantially chemically inert to the reaction conditions utilized, as discussed before for the containers. The solid support preferably swells in the solvents utilized during the synthesis due to physical, rather than chemical processes.

The solid supports typically fall into one of three general types, each of which is discussed below.

Perhaps the most utilized particles for polypeptide and oligo- and polynucleotide syntheses are polymerized resins. The polymerized resins are generally in the form of porous beads.

Of the resins, the hydrophobic polymerized styrene cross-linked with divinyl benzene (typically at about 0.5 to about 2 weight percent) resins are the most often utilized, especially for polypeptide syntheses. The resin beads so prepared are further reacted to provide a known quantity of a benzyl moiety as a portion of the polymerized resin. The benzyl moiety contains a reactive functional group through which the subunits of the sequence to be synthesized may be covalently linked by a selectively severable bond. Although the reactive benzyl moieties are typically added after the resin bead has been synthesized by reaction of a polymerized styrene moiety, such resins are herein generally described as polymerized styrene cross-linked with divinyl benzene and including a known amount of polymerized vinyl benzyl moiety.

The reactive functionality of the benzyl moiety is typically selected from the group consisting of aminobenzyl and halobenzyl such as chlorobenzyl. Polymerized, cross-linked styrene resins containing chlorobenzyl moieties are sometimes referred to in the art as chloromethyl styrene resins, while resins containing aminobenzyl moieties are sometimes referred to as amino-styrene or aminomethyl-styrene resins.

It is noted that the subunit/particle link formed between a particle containing aminobenzyl moiety and a carboxylic acid is not readily cleavable under usual conditions of synthesis. As a consequence, such particles are used with severable linking groups between the particle and first linked subunit, where a free subunit reaction product is desired to be recovered.

Additional useful resin particles are those materials referred to by East et al., *J. Immunol.*, 17, 519–525 (1980) as macroreticular resins. Those resins are said to be prepared from cross-linked polystyrene and to include a reactive aminobenzyl moiety. The described resin particles contain pores of a large enough cross-section to permit entry of antibodies and immunoreaction of those antibodies with the synthesized polypeptide. The macroreticular resins were reported to be obtained from Rohm & Haas under the trademark designation XE-225A.

Resins containing a known amount of chlorobenzyl moieties may be purchased from Sigma Chemical Co., St. Louis, Mo. under the trademark names Merrifield's Peptide Resin (chloromethylated co-polystyrene divinylbenzene). Such materials are typically supplied containing about 0.1 to about 2 milliequivalents of chlorine per gram of particle.

The aminobenzyl group may be prepared from polymerized styrene cross-linked with divinyl benzene by reaction with N-(hydroxymethyl)phthalimide under Friedel-Crafts conditions followed by hydrazinolysis of the phthalimide group as is described by Kent Merrifield, *Israel J. Chem.*, 17, 243–247 (1978). Particles containing reactive aminobenzyl moieties are also commercially available from Pierce Chemical Company of Rockford, Ill. and are reported to contain about 0.3 to about 0.7 millimoles of aminobenzyl moiety per gram of particles.

Intermediate linking groups between the reactive benzyl moiety and the first of a sequence of subunits may also be employed as is the case of the 4-(oxymethyl) phenylacetyl group bonded to an amino benzyl moiety reported by Kent and Merrifield, above. Another linking group is the 4-(oxymethyl)phenoxy group bonded to a benzyl moiety as reported by Meienhofer et al., *Int. J. Peptide Protein Res.*, 13, 35–42 (1979).

The above-described polystyrene-based particles are frequently used in the synthesis of polypeptides in which the carboxyl-terminal amino acid residue (subunit) is bonded through a selectively severable covalent bond to the polymerized, reactive vinyl benzyl moiety of the resin. Benzyl ester bonds between the polystyrene-based particle and subunit are stable in the presence of relatively mild acids, but sever when treated with strong acids such as hydrofluoric acd or a mixture of acetic and hydrobromic acids. Polypeptide syntheses are typically carried out using mild acid-sensitive protecting groups on the alpha amino groups such as N-tert-butoxycarbonyl (BOC), while using other, strong acid-sensitive protecting groups on reactive side chains.

One of the difficulties in working with large quantities of synthetically prepared polypeptides relates to the usual practice of using anhydrous hydrogen fluoride (HF) to sever the synthesized polypeptide reaction product and its side chain protecting groups from the solid support. Hydrogen fluoride is not an easy material to work with and must be handled with great care. In addition, since HF severs both the polypeptide from the particle and side chain protecting groups from the polypeptide, the severed polypeptide must be purified from the side chain protecting groups.

A newly developed disulfide-containing linking group that may be bonded to a benzylamine of a before-described resin particle may be utilized to alleviate some of the difficulties encountered in using HF to sever the polypeptide reaction product and to remove side chain protecting groups. A precursor to that linking group is represented by the formula:

BOC—NHCH$_2$CH$_2$SSCH$_2$(CH$_2$)$_x$CO$_2$H wherein BOC is tert-butoxycarbonyl, and x is a numeral having the value of zero or one, such that when x is zero, the parenthesized CH$_2$ group is absent.

The carboxyl group of the linking group is bonded to the amino group of a polymerized vinyl benzyl moiety of a reactive resin-containing particle using standard peptide amide bond-forming techniques such as via the anhydride or with dicyclohexylcarbodiimide. The BOC group is thereafter removed using mild acid as is well known, the resulting ammonium salt is neutralized to provide a free primary amine and the resulting free primary amine-containing particles are rinsed to remove any excess base-containing reagent used in the neturalization step.

The first amino acid subunit is thereafter coupled through its carboxylic acid group to the free primary amine to form a particle-linked subunit. The amino acid residue is linked to the resin through an amide bond between the carboxyl group of the amino acid and the amino group of the disulfide-containing linking group that is itself bonded by an amide bond to the polymerized vinyl benzyl moiety of the resin. The resulting linking group, written in the direction from left to right and from the amino acid residue toward the benzyl moiety, is represented by the formula:

—NHCH$_2$CH$_2$SSCH$_2$(CH$_2$)$_x$CONH— where x is as before-described.

The linking group with any amino acid that may be designated "Z" coupled through its carboxyl group and with the particle bonded through its polymerized vinyl benzyl moiety may be written as described above:

Z—NHCH$_2$CH$_2$SSCH$_2$(CH$_2$)$_x$CONH—Particle.

A particular benefit of using the above-described linking group is that its amide and disulfide bonds are stable to contact with HF and other strong acids used to selectively remove amino acid side chains. Consequently, such acids may be used to remove the side chains of the polypeptide reaction product while that reaction product is still linked to the resin particle. That selective removal permits the removed side chain protecting groups to be rinsed away from the reaction product-linked resin particle and thereby provides easier purification of the polypeptide reaction product.

The polypeptide-linked resin particle is thereafter contacted with a disulfide bond-breaking agent to selectively sever the polypeptide reaction product from the resin particle. The severed polypeptide reaction product may thereafter be recovered in relatively pure form using standard procedures such as extraction of the severed reaction product/particle mixture formed with an aqueous composition containing 5% acetic acid. The extracted composition may thereafter be lyophilized to provide the reaction product. The reaction product may also be further purified as is known prior to its ultimate recovery.

Several reagents are well known to be useful for breaking the disulfide bond. Exemplary reagents include sodium borohydride, 2-mercaptoethanol, 2-mercaptoethylamine, dithiothreitol and dithioerythritol. Mercaptan-containing carboxylic acids having two to three carbon atoms and their alkali metal and ammonium salts are also useful. Those reagents include thioglycolic acid, thiolactic acid and 3-mercaptopropionic acid. Exemplary salts include sodium thioglycolate, potassium thiolactate, ammonium 3-mercaptopropionate and (2-hydroxyethyl)ammonium thioglycolate.

The disulfide-containing BOC-protected linking group precursor may be prepared by standard techniques. For example 2-aminoethyl disulfide may be reacted with two moles of 2-(tert-butoxycarbonyloxylmino)-2-phenylacetonitrile or N-(tert-butoxycarbonyloxy)phthalimide or a similar reagent to form bis-N-BOC-2-aminoethyl disulfide. That disulfide may then be reacted with thioglycolic acid or 3-mercaptopropionic acid to form the precursor shown above.

A relatively newer group of resin particles has been reported by E. Atherton and co-workers. Those particles are based upon copolymers of dimethyacrylamide cross-linked with N,N'-bisacryloylethylenediamine, including a known amount of N-tert-butoxycarbonyl-beta-alanyl-N'-acryloylhexamethylenediamine. Several spacer molecules are typically added via the beta alanyl group, followed thereafter by the amino acid residue subunits. See Atherton et al., *J. Am. Chem. Soc.*, 97, 6584–6585 (1975).

More recently still, Atherton and co-workers have reported on the replacement of the beta alanyl-containing monomer with an acryloyl sarcosine monomer during polymerization to form resin beads. The polymerization is followed by reaction of the beads with ethylenediamine to form resin particles that contain primary amines as the covalently linked functionality. See Atherton et al., *Bioorg. Chem.*, 8, 351–370 (1979) and Atherton et al., *J.C.S. Perkin I*, 538–546 (1981).

The polyacrylamide-based resin particles are relatively more hydrophilic than are the polystyrene-based resin particles and are usually used with polar aprotic solvents. Exemplary solvents include dimethylformamide, dimethylacetamide, N-methylpyrrolidone and the like.

Atherton and co-workers and others have also reported polypeptide syntheses that use the base-sensitive alpha amine protecting group N-9-fluorenylmethyloxy carbonyl in conjunction with the polymerized dimethylacrylamide-based resins. See Atherton et al., *J.C.S. Perkin I*, 538–546 (1981) and Meienhofer et al., *Int. J. Peptide Protein Res.*, 13, 35–42 (1979).

A second group of solid supports is based on silica-containing particles such as porous glass beads and silica gel. For example, Parr and Grohmann, *Angew. Chem. internat. Ed.*, 11, 314–315 (1972) reported on the use of the reaction product of trichloro-[3-(4-chloromethylphenyl]propyllsilane and porous glass beads (sold under the trademark PORASIL E by Waters Associates, Framingham, MA) as solid support for polypeptide syntheses. Similarly, a mono ester of 1,4-dihydroxylmethylbenzene and a silica (sold under the trademark BIOPAK by Waters Associates) was reported to be a useful solid support for polypeptides syntheses by Bayer and Jung, *Tetrahedron Lett.*, 4503–4505 (1970). Each of the above solid supports is seen to utilize a reactive benzyl moiety through which the subunit was bonded to the particle.

The third general type of useful solid support may be termed composites in that they are constituted by two major ingredients, a resin and another material that is also substantially inert to the organic synthesis reaction conditions employed.

One exemplary composite reported by Scott et al., *J. Chrom. Sci.*, 9, 577–591 (1971) utilized glass particles coated with hydrophobic, polymerized, cross-linked styrene containing reactive chloro methyl groups and was supplied by Northgate Laboratories, Inc., of Hamden, CT. Another exemplary composite was reported to contain a core of fluorinated ethylene polymer onto which was grafted linear polystyrene. See Kent and Merrifield, before, and van Rietschoten, in *Peptides 1974*, Y. Wolman ed., Wiley and Sons, New York, 113–116 (1975).

Similar solid supports are also reported for synthesis of oligo- and polynucleotides. For example, Letsinger and Mahadevan, *J. Am. Chem. Soc.*, 87, 3526, (1965) reported on the use of a so-called "popcorn" cross-linked styrene copolymer; Duckworth et al., *Nucleic Acids Research*, 9, 1691–1706 (1981) reported on the use of succinylated amine-containing polydimethylacrylamide-based resins; Protapov et al., *Nucleic Acids Research*, 6, 2041–2056 (1979) reported on the use of a composite solid support based on a polytetrafluoroethylene core containing grafted polystyrene; and Matteucci and Caruthers, *J. Am. Chem. Soc.*, 103, 3185–3190 (1981) reported the use of macroporous silica gel reacted with (3-aminopropyl)triethoxy silane.

General reviews of useful solid supports (particles) that include a covalently linked reactive functionality may be found in Atherton and Sheppard, *Perspectives in Peptide Chemistry*, Karger, Basel, 101–117 (1981) and in Amarnath and Broom, *Chem. Rev.*, 77, 183–217 (1977).

2. Particles With Pre-Reacted Subunits

A synthesis means of this invention may also be provided as a previously described container that encloses a known amount of particles having a known amount of organic synthesis subunits linked thereto by selectively severable covalent bonds. Each of such subunits that is farthest from (distal to) the particle/subunit link contains a functional group capable of reacting during the organic synthesis but that is protected from so reacting by a selectively removable, covalently linked protecting group.

Illustratively, 5'-O-dimethoxytrityl-protected nucleosides linked to particles by 3'-O-succinyl linkages are commercially available from Biosearch of San Rafael, CA. Those commercially available particles are available wherein the succinyl linking groups are also bonded to (a) 20–60 micron silica particles by (3-aminopropyl)diethoxysiloxane groups; (b) supports of polymerized styrene cross-linked with either 1 or 2 percent divinyl benzene that include polymerized vinyl aminobenzyl moieties (also referred to as amino-polystyrene); and (c) 10 percent cross-linked polydimethylacrylamide-based resins that include glycylethylenediamino linkages (also referred to as amino-polydimethylacrylamide). The nucleosides of such particles also typically include appropriate protecting groups for the ring substituents such as N-benzyl and N-isobutyl protecting groups, as are well known.

Particle-linked, selectively severable subunits that themselves contain protected reactive functional groups are provided in known amounts lnked to the particles by the manufacturer. For example, Sigma Chemical Company, provides protected, nucleoside-containing particles prepared from a resin similar to the before-described succinylated amino-polystyrene resin that contain 0.1 to 0.2 millimoles of nucleoside per gram of particle.

Similarly, resin particles of polymerized styrene cross-linked with divinyl benzene and including a known amount of polymerized vinyl benzyl moiety that contain linked amino acid residue subunits having protected reactive functionalities such as N-tert-butoxycarbonyl-protected alpha amino (BOC-protected) groups are provided by several suppliers. Exemplary of such suppilers are Applied Biosystems, Inc. of Foster City CA, Vega Biotechnologies, Inc. of Tucson AZ and Chemical Dynamics of Rahway NJ. Each particulate material is supplied with a statement as to the amount of linked amino acid residue present in the particles.

The particles of the synthesis means described before in this section each had a plurality of a single organic synthesis subunit linked to it. Those subunits such as a 5'-dimethoxytrityl-protected nucleoside or BOC-protected amino acid residue being the only subunit linked to the particle are also per force, the subunits farthest (distal) from the particle/subunit link.

This invention also contemplates individual synthesis means enclosing particles that contain identical sequences of two or more reacted subunits (reaction products) that are linked to the particles by one selectively severable covalent bond per sequence. Such particles thus contain a reacted subunit that is linked to the particle; i.e., that is proximal to the particle, and a subunit that is farthest from the particle; i.e., that is distal to the particle. Since both single subunits linked to the particles and subunit-containing reaction product sequences linked to the particles contain distal subunits, both types of particles are usually referred to hereinafter as subunit-linked particles, and the subunits and reaction product sequences are usually referred to as particle-linked subunits.

C. Methods

The synthesis means of the present invention are utilized in methods for the solid phase preparation of reaction products that contain a sequence of reacted subunits that are chemically similar such as amino acids or nucleic acids used to prepare polypeptides and oligo- or polynucleotides, respectively. Those preparations may utilize the naturally occurring subunits such as the twenty L-alpha amino acids and five sugar-linked bases usually found in RNA and DNA sequences.

However, the methods of this invention are not limited to the use of naturally occurring subunits. For example, appropriately protected D-alpha amino acids, achiral amino acids such as beta alanine or 4-aminobutyric acid and synthetic nucleic acid derivatives such as 5-flurouridine may be used as subunits in syntheses of polypeptides, and oligo- and polynucleic acids, respectively.

The methods of carrying out sequential, solid phase organic syntheses also constitute an aspect of this invention. Those syntheses may begin with a container that encloses reactive particles that contain a reactive functionality or particles having selectively severable, covalently linked subunits that include a selectively removable protecting group covalently linked to a subunit reactive functional group. In addition, the synthesis means may be used individually for each synthesis, or an admixture of a plurality of such means may be utilized.

It has been surprisingly found that when a synthesis means of this invention is utilized singly in the synthesis of a polypeptide, the yield of the desired, ultimately obtained polypeptide was greater than that obtained by using the standard, Merrifield-type synthesis in which the resin particles were free in the reaction reservoir. The reason for the noted improvement in yield is unknown.

However, without wishing to be bound by a single hypothesis, it is believed that the increase in yield was due to the fact that some resin particles of the Merrifield-type synthesis became adhered to the reservoir walls and were therefore not adequately contacted by the reaction solutions. Since the synthesis means are relatively large and heavy entities as compared to individual resin particles, the synthesis means did not become adhered to the reservoir walls, and were therefore easily contacted by each of the reaction solutions, thereby assuring that each of the particles therewithin was adequately contacted and bathed by those solutions.

Turning first to synthesis methods utilizing a single synthesis means, it is noted that methods utilizing a container enclosing reactive particles that contain a reactive functionality and those utilizing a container enclosing particles having selectively severable, covalently linked subunits that include a selectively removable protecting group covalently linked to a subunit reactive functional group may be similar for several embodiments. Indeed, the latter methods may be encompassed within the former methods. Thus, only the former method will be discussed hereinbelow.

In accordance with that method, a synthesis means as described hereinbefore is provided. That means includes a container that encloses reactive particles that contain a reactive functionality. It is to be understood that each particle typically contains a plurality of reactive functionalities.

First subunits such as an amino acid or nucleoside derivative are reacted with the reactive functionalities to form a selectively severable covalent bond between the first subunits and the particles to thereby form a synthesis means that contains particle-linked subunits. The first subunits include a first functional group that reacts with the reactive functionality of the particles and a second reactive functional group that is protected from reaction by a selectively removable, covalently bonded protecting group such as BOC or dimethoxytrityl. Other reactive groups that may be present on the subunit such as the reactive amino acid side chains, amino or hydroxyl groups of nucleic acid bases and sugars are also covalently bonded to selectively removable protecting groups that are not removed by the reactions of the sequential syntheses.

The protecting groups of the second-named reactive functional groups are removed as by contact with a mild acid solution to form a synthesis means containing particle-linked subunits having free reactive functional groups. For sequential syntheses involving alpha amino acids, the free reactive functional groups are amines. For nucleotide syntheses the reactive functional groups are 5'-hydroxyl groups.

Treatment of a BOC-protected amino group with acid to free the amine forms an ammonium salt (protonated amine). The amine-bound proton is removed to form the free reactive functional group (free primary amine) by reaction of the ammonium group with a liquid composition containing a base such as di-isopropylethylamine or triethylamine. That step is typically followed by separation of the resulting solid/liquid phase admixture and one or more rinse steps, with attendant separations, to provide the free reactive functional group.

The synthesis means containing its particle-linked subunits having free reactive functional groups is then admixed with an excess of identical, known other subunits that contain (i) a functional group such as a carboxyl or phosphatyl group that is capable of reacting with the free reactive groups of the particle-linked subunits, and (ii) a second functional group such as an alpha amine or a 5'-hydroxyl that is covalently linked to a selectively removable protecting group such as a BOC or trityl group.

As is known, the excess of subunit admixed may vary from about 0.1 mole to twenty or more moles. More typically, an excess of about 3 to about 10 moles over the amount of free reactive functional group is utilized.

The particle-linked free reactive groups and the admixed functional groups are reacted to form covalent bonds (coupled) such as peptide and phosphate bonds, and thereby form particle-linked subunit reaction products. Those reaction products contain a selectively removable protecting group on the subunits distal from the particle/subunit linkages.

The bond-forming reaction between the particle-linked free reactive functionality and the admixed subunit reactive functional group proceeds by means of an activated bond, typically on the admixed subunit. In the specific emodiments described herein, that activated bond is in an amino acid anhydride that is admixed with the synthesis means. Other subunits containing activated, reactive functional groups inclue p-nitrophenyl and N-hydroxysuccinimido esters of amino acids. Bond activation may also occur in situ through the use of a carbodiimide such as dicyclohexylcarbodiimide and the like as are well known.

Unreacted subunits are separated from the particle-linked reaction products. Such separations are well known solid/liquid phase separations. The separation is typically followed by one or more rinses.

After that separation and rinsing, where used, the protecting groups of the subunits distal from the particle/subunit linkage are selectively removed to form further particle-linked reaction products containing free reactive functional groups. Where the distal protecting groups are the same as those present on the first subunit, the same removal steps are employed, including the before-discussed neutralization and rinse steps for polypeptide syntheses.

Thereafter, steps analogous to the above steps of admixing identical, known reactive subunits, coupling those subunits to the particle-linked subunits, separating excess, uncoupled subunits and deprotecting the distal protecting groups are repeated serially until particle-linked reaction products containing the desired number and identity (sequence) of reacted subunits are synthesized.

Once the desired particle-linked subunit reaction product sequence is synthesized, the selectively severable bond between the first-named subunits and the particles is severed to form free reaction products and reacted particles. As noted previously, that severance is normally accomplished for polypeptides using a strong acid such as anhydrous hydrofluoric acid (HF) that is condensed from the gas phase into a reaction vessel containing the synthesis means. It is also noted that side chain protecting groups are also removed at this step where HF is used.

The severed, free reaction product sequences are separated from the reacted particles. This step is typically carried out by extraction using an aqueous composition that contains about 5 to aobut 50 percent acetic acid.

The separated, free reaction product subunit sequences are thereafter recovered. Recovery techniques are well known in the art and include drying of the extract as by freeze drying, passage over desalting columns followed by drying, and the like.

The invention further contemplates use of a plurality of synthesis means each of which encloses a known amount of particles that have a known amount of organic synthesis subunits present as single subunits or as a sequence of reacted subunits (subunit reaction products), with the distal subunit of each particle containing a reactive functional group capable of reacting during the organic synthesis but that is protected from so reacting by a removable, covalently linked protecting group. Each of the plurality of synthesis means may enclose subunits or reaction products that are the same, or that are different. However, the subunits or reaction products within each of the synthesis means are the same. The specific example that follows, illustrates this method by simultaneously covalently bonding a subunit of one identity to each of a plurality of particle-linked distal subunits, present as a single subunit or as a subunit reaction product, without intermingling subunit-linked particles.

In accordance with that method, an admixture is provided that contains a plurality of the before-described synthesis means that enclose subunit-linked particles in which each subunit that is distal from the particle/subunit link contains a reactive functional group capable of reacting during the organic synthesis, but that is protected from so reacting by a selectively removable, covalently linked protecting group. In some embodiments illustrated hereinafter, the particles have identical subunits or subunit reaction products linked to them, while in other embodiments, the subunits or reaction product sequences differ so that the chemical identity of the linked subunits differ.

The protecting group bonded to the distal reactive group is selectively removed to form an admixture containing a plurality of synthesis means that enclose particle-linked subunits having free reactive groups. For example, the alpha amino BOC or 5'-O-dimethoxytrityl groups are removed from all of the particle-linked subunits of the admixture.

In the case of the BOC amino-protecting groups, that removal is accomplished by contacting all of the enclosed, protected particle-linked subunits with a liquid composition that contains a relatively mile acid, e.g., an acid that will not cleave the subunit/particle links, followed by separating the solid and liquid phases, a neutralization step with a liquid, base-containing composition to provide the alpha amine in free base form, a further solid/liquid phase separation step, one or more rinses to remove the base, and separating of the solid and liquid phases after each rinse.

The free reactive group-containing admixture so formed is admixed with an excess of identical subunits to form a new admixture. Each of those subunits contains (i) a second reactive functional group capable of reacting with the free reactive group of the particle-linked subunits, and (ii) reactive groups identical to the first-named, free reactive functional groups, formed above, that are protected from reacting by selectively removable protecting groups. Typically, those last-named selectively removable protecting groups are the same as the first-named protecting groups; i.e., BOC and 5'-O-dimethoxytrityl.

Covalent bonds are formed between the free reactive groups of the particle-linked subunits and the second reactive groups of the admixed subunits to couple the admixed subunit to the particle and form an admixture of a plurality of synthesis means that enclose particle-linked subunit reaction products whose distal subunits (last-bonded subunits) contain selectively removable, protected reactive functional groups.

In the specific embodiment that follows, the admixed, identical subunits are BOC-protectd alpha amino acid anhydrides. However, similar BOC-protected or otherwise protected alpha amino acids in acid form may be admixed and the covalent bonds formed as described before.

DCC is well known to be useful for forming covalent bonds between the 5'-hydroxyl group of particle-linked nucleosides and nucleotides with the 3'-phosphate groups of 5'-O-protected nucleic acid subunits. Use of activated phosphate esters analogous to the activated carboxylate esters are also well known in the art.

The admixed, unreacted subunits are separated form the particle-linked reaction products of the admxiture of synthesis means, as discussed before.

Thereafter, the synthesis means of the admixture are separated from each other, and the linked reaction products recovered as already described. That separation may occur after only one subunit has been added to the reaction product sequence, or one or more identical further subunits may be added to each reaction product prior to that separation.

It is important to note that by using the above method, the same subunit is simultaneously added to each of the subunits enclosed within each of the synthesis means containers. Since each of the containers is separated from the other containers, their enclosed subunit-linked particles do not intermingle, but are physically separated from each other.

The specific embodiment disclosed in the following section may be used as exemplary of the improvement provided by the present invention. There, it was desired to synthesize analogs of a thirteen-residue polypeptide corresponding to positions 98–110 from the amino-terminus of a hemagglutinin molecule of the influenza virus, with the amino acid residue sequence, from left to right, in the direction from amino-terminus to carboxy-terminus, and using the single letter amino acid code, that corresponds to the sequence: YPYDVP-DYASLRS. The analogues desired contained twelve residues of the preceding sequence with a thirteenth residue corresponding to each of the twenty naturally occurring amino acids, as point variations. Since point variations were desired at each of the thirteen positions of the sequence, a total of 160 sequences were required. If done following usual, one at a time, Merrifield-type syntheses, the preparation of all 160 sequences would have taken about six months with the equipment and personnel available. Using the synthesis means and methods of this invention, those 160 polypeptides were prepared in less than one month.

The synthesis in which with the leucine residue (108 from the amino-terminus) was changed to each of the other 19 amino acid residues may be used as exemplary of the total syntheses performed and of the general method. To accomplish the syntheses, twenty synthesis means made of material inert to the reactants and solvents used in solid phase peptide synthesis (e.g., polypropylene, polyethylene, etc.) each enclosing a given quantity of a particle-linked, alpha amine-protected amino acid residue (e.g., 50 mg of BOC-Ser-resin) were provided. The particles used were resin beads fabricated of polymerized styrene cross-linked with divinyl benzene and containing polymerized vinyl benzyl moieties. The synthesis means were placed in one reaction vessel, and all the steps of the various syntheses were carried out identically except for the coupling steps used to add the amino acid residues at the variation point of interest; i.e., 108-Leu.

For the coupling at the variation point, the 20 different synthesis means were separated from each other and removed from the reaction vessel following selective removal of the protecting group of the distal residue [the BOC of the particle linked arginine (R) of the BOC-RS sequence]. The individual synthesis means were then placed into different containers separately holding each of the twenty activated amino acids of interest (BOC amino acid anhydrides). The reactive carboxyl group of each of those amino acids was then bonded to the free amino groups on each of the particle-linked dipeptide reaction products to form tripeptide-linked reaction products having a distal protected reactive group (BOC-alpha amine). Excess, unreacted, activated amino acids were separated from each of the synthesis means, and each synthesis means was typically rinsed to assure removal of unreacted, activated amino acid.

It is noted that deprotection and freeing of the protected arginine alpha amino group prior to the coupling step need not be carried out prior to the separation and removal of the individual synthesis means. Those steps may be carried out in each of the reaction vessels used to add the differing amino acid residues.

Following the addition of the varying amino acid subunits, the synthesis means were returned to a single reaction vessel, and the synthesis was continued until its completion for the entire 13-subunit sequence. The polypeptides were then separately severed from the resin using standard procedures, and were purified, characterized, and used in enzyme-linked immunosorbant assays.

It is apparent that this method may also be similarly used if a variety of totally different peptide sequences are desired, and that it is not limited to polypeptide antigens. For example, if a worker were synthesizing ten different polypeptides, each of which required a glycine residue at some position in its sequence, glycines could be added to each of the ten sequences using only one set of deprotection, neutralization, and coupling steps, rather than ten sets of such steps. After the glycine was added, one or more of the synthesis means may be removed and another, particular amino acid residue added to those reaction product sequences that required the particular amino acid residue to be bonded to an amino group of glycine, and so on.

The methods of this invention may also be carried out on a still larger scale in which hundreds of synthesis means are utilized per synthesis. When relatively large numbers of synthesis means, e.g., about 25 to one hundred or more, are utilized at one time, it is frequently convenient to group together synthesis means containing related reaction products. A device for making such groups is shown in FIG. 5.

Figure 1:
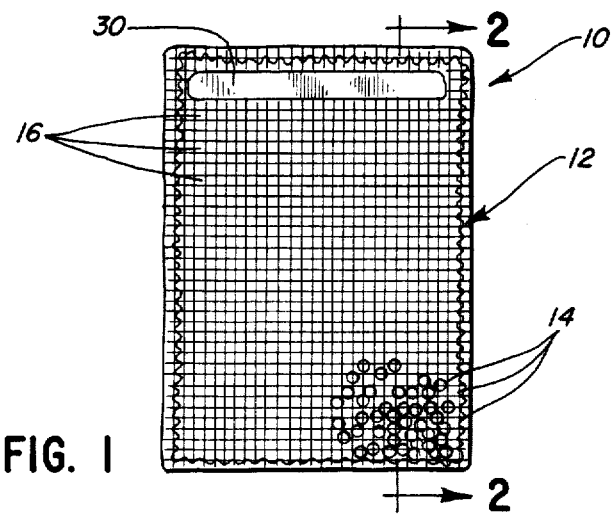
FIG. 1 is an enlarged plan view of a synthesis means of this invention.
Figure 2:
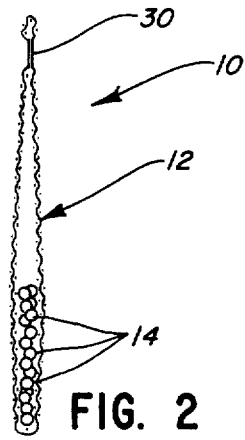
FIG. 2 is a cross-sectional view of the synthesis means of FIG. 1 taken along line 2—2 in FIG. 1.
Figure 3:
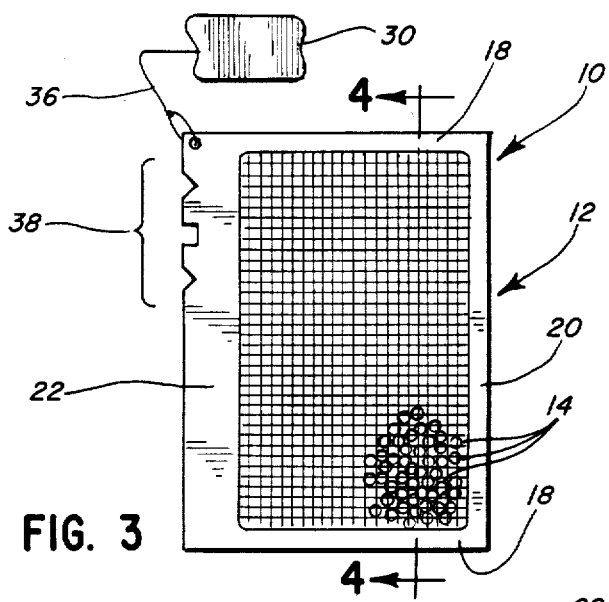
FIG. 3 is an enlarged plan view of another embodiment of a synthesis means of this invention.
Figure 4:
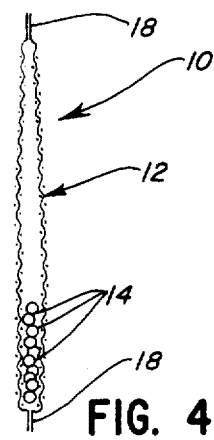
FIG. 4 is a cross-sectional view of the synthesis means of FIG. 3 taken along line 3—3 in FIG. 3.
Figure 5:
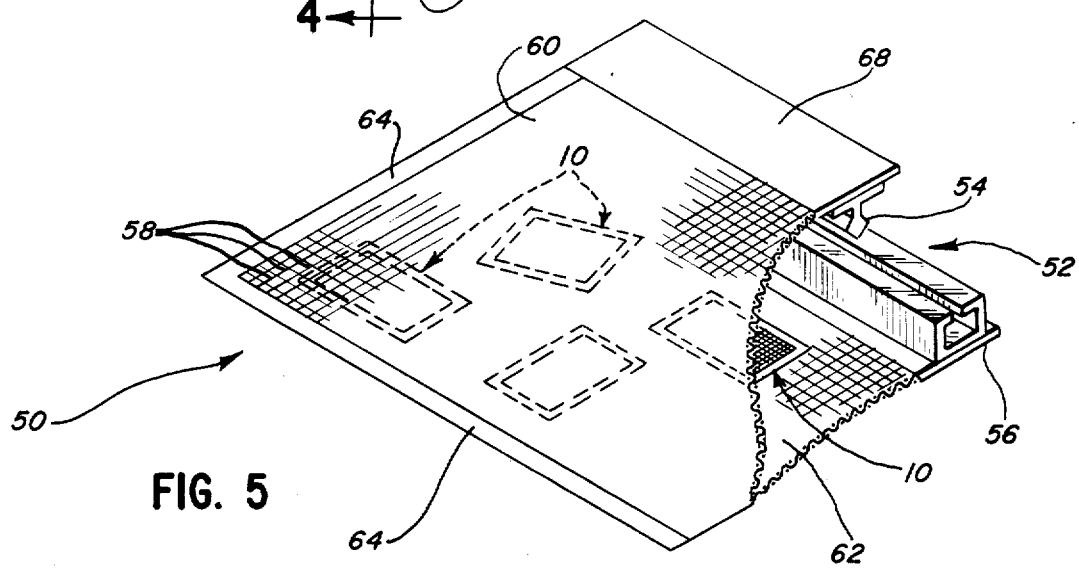
FIG. 5 is an enlarged, partially cutaway perspective view of a resealable, permeable synthesis means envelope and its contained synthesis means.

The device of FIG. 5 is generally designated by the numeral 50 and is a foraminous container or envelope that includes a resealable closure means 52. The envelope 50 is preferably of a generally rectangular shape and is comprised of first 60 and second 62 opposing webs, at least one of which is foraminous.

The webs 60 and 62 are partially secured together at their peripheries such as by heat sealing at 64, with each web further secured to resealable closure means 52 whereby the closure means defines a mouth of the envelope 50 which communicates with the interior therof.

The resealable closure means is comprised of a male element 54 and a female element 56 that matingly engage and cooperate to close the envelope when those elements are pressed together in a face-to-face relation. As shown in FIG. 5, the male and female elements 54 and 56 are preferably in a generally parallel, superimposed relation.

The first web 60 is operably connected to the male element 54 adjacent the mouth 66 of the envelope 50. The second web 62 is operably connected to the female element 56 adjacent to the envelope mouth. The webs 60 and 62 and closure means 52 are preferably fabricated from polymers of propylene, ethylene or mixtures thereof. The webs are preferably connected to the respective elements 54 and 56 of the closure means by heat sealing.

Exemplary closure means are illustrated in U.S. Pat. No. 4,354,541 whose appropriate disclosures are incorporated herein by reference. The so-called hook and loop fastening means of U.S. Pat. No. 3,009,235, whose disclosures are also incorporated herein by reference, are also useful in which use the hook portions correspond to the male element 54 while the loop portions correspond to the female element 56 of the closure means. The male and female matingly engagable closure means of plastic bags sold under the trademark ZIP LOCK by Dow Chemical are also useful herein.

The envelope and its closure means are made of materials that are substantially chemically inert to the reaction conditions utilized in the sequential organic synthesis. Again, materials made from polymerized ethylene, propylene and their mixtures are preferred. A surface capable of bearing identifying indicia such as at 68 is also preferably included.

The foraminae 58 defined by webs 60 and 62 of the envelope 50 are at least equal in size to the size of the foraminae 16 defined by each of the plurality of individual synthesis means 10 positionable with envelope 50, and are preferably larger, but not so large that the individual synthesis means 10 may pass through them. Thus, the foraminae 58 are sized large enough to allow drainage of fluids such as solvents used in the synthetic reactions within a period of 5 minutes at the synthesis temperature, while retaining the individual synthesis means 10 within the envelope; i.e., the foraminae are small enough to prevent the passage of a synthesis means therethrough.

A number of generably rectangular envelopes have been prepared using woven polypropylene cloth having generally square mesh interstices of about 0.5 millimeters per edge as the webs 60 and 62 of the envelope. The closure means 52 from a ZIP LOCK bag was cut from the the remainder of that bag. The male element portion 54 of the closure means was heat sealed to first envelope web 60, with the female element portion 56 of the closure means being heat sealed to the second web 62.

The two webs 60 and 62 were then secured by heat sealing along their peripheries at 64 to provide a substantially continuous closure means around three edges of the envelope.

In practice, an admixture of synthesis means 10 is provided. Of that admixture of synthesis means 10, some or all of the synthesis means 10 may be placed into one or more foraminous envelopes 50. One or more of the synthesis means 10 of the admixture may also be provided for simultaneous synthesis, but not positioned in the foraminous envelope 50. Thus, a portion of the admixture of synthesis means 10 may be positioned within the foraminous envelope 50. This is shown in FIG. 5 wherein the envelope contains four synthesis means. The envelope is then sealed as by pressing the male 54 and female 56 elements into mating engagement.

A new admixture may be formed that contains at least one envelope containing a plurality of synthesis means and additional synthesis means. The additional synthesis means may be free, or all or a portion of them may be enclosed in one or more additional envelopes. The new admixture is admixed with identical subunits to be coupled to the particles of the synthesis means, including particle-linked reaction product, and that subunit is coupled as preveiously described.

Where a particular reaction product is to contain a different subunit sequence from the others in the envelope and new admixture, the envelope is unsealed, the desired synthesis means is separated from the others in the envelope, and is removed from the envelope. The subunits of removed synthesis means are then reacted as desired, and the synthesis means may be placed back into the envelope. The envelope is resealed, and one or more further subunit additions or other reactions are carried out.

More specifically, the 160 related sequences discussed before may be prepared in 13 envelopes containing twenty synthesis means per envelope. At the synthesis step at which 108-Leu, for example, is to be added, 11 envelopes contain synthesis means whose reaction products have the sequence BOC-RS-particle, one envelope contains the reaction sequence BOC-ZS-particle, and another BOC-RZ-particle; where Z is one of the twenty naturally occurring amino acid residues.

One of the eleven envelopes with the BOC-RS-particle reaction product sequence is then separated from the other twelve envelopes. It is opened, its synthesis means are separated and removed, and each is separately reacted with each of the twenty natural amino acids to form the sequence BOC-ZRS-particle, where Z is as above.

The other twelve envelopes are reacted together in a single vessel to add the desired 108-Leu residue. Thereafter ten of those reaction product sequences have the sequence BOC-LRS-particle, one subunit reaction product has the sequence BOC-LZD-particle, while the last envelope contains subunit sequence reaction products having the sequence BOC-LRZ-particle, where Z is as before-defined.

One of the ten envelopes with the sequence BOC-LRS-particle is thereafter withdrawn from the vessel. It is opened, its synthesis means are separated and removed, and are reacted separately to couple each of the twenty amino acids to its sequence. The individual synthesis means whose sequences are BOC-ZRS-particle are returned to their envelope, and that envelope and the remaining eleven envelopes are placed into a single reaction vessel. The next subunit amino acid residue of the sequence, serine (S) is coupled to the subunit reaction product sequences within all of those eleven envelopes.

The above-described synthetic procedure illustrates one embodiment of what may be termed a "multiple analog peptide synthesis (MAPS)."

In another more specific method, related or unrelated sequences may be prepared by providing twenty envelopes, one for each of the usual twenty amino acids. In carrying out this method, a plurality of the before-described synthesis means, each bearing an identifying indicia, is placed into the one of twenty envelopes designated to be used where one of the twenty amino acid residues is to be added to synthesis means particles.

The desired subunit is then added to the particles of each synthesis means following the previously described methods. After that addition, and preferably prior to the deprotection step, the synthesis means are removed from the envelope and sorted as to the identity of the next subunit to be added.

Those synthesis means to which the same, next subunit are to be added are grouped together and placed into one or more appropriate envelopes. The next subunits are then added to all of the particles of the synthesis means of a given envelope following deprotection and the other usual steps that may be suitable for the type of sequence, e.g., polypeptide or polynucleotide, that is being prepared.

It is noted that the indicia on the synthesis means and envelopes may be readable by a human, as where numerical or letter indicia are utilized. However, machine-readable codes such as a code of lines, a binary code of zeros and ones as read by a digital computer, a code based upon cut out shapes as shown at 38 in FIG. 3, and the like may be utilized.

It is thus seen that the same subunit may be added to a few to hundreds of polypeptide sequences that are unrelated using the envelopes of this invention to hold and group synthesis means that receive like subunits added to their subunit sequences. This type of synthesis may be referred to as a simultaneous multiple peptide synthesis (SMPS) since a plurality of different polypeptides is synthesized, at least as to a particular subunit, together, at one time.

Steps similar to those described above may be carried out until all of the 160 sequences are prepared. The discussion in Section II that follows further illustrates the invention.

II. Specific Embodiments of the Invention

A. Results

1. Polypeptide Synthesis

A replacement series of 248 polypeptides and 13 controls for the 13 amino acid sequence corresponding to residues 98–110 of the hemagglutinin molecule, HA1, were prepared, as were 13 omission analogs missing a single amino acid at each position in the polypeptide, and a replacement series in which each naturally occurring L amino acid was replaced by its D-isomer. FIGS. 1–4 illustrate the type of synthesis means used in their preparation.

Using such synthesis means, a total of 286 individual polypeptides were synthesized for a total of more than 3700 coupling steps. For the principal 247 polypeptides plus 13 duplicates, or 260 polypeptides, more than 3380 coupling steps were utilized. Each polypeptide was obtained in 10–20 milligram (mg) quantities.

The purity of these polypeptides was excellent as shown by the amino acid analyses of the replacement series that were typically within 10 percent of the theoretical values. Similarly, high pressure liquid chromatography (HPLC) chromatograms gathered on the crude polypeptides indicated no cross-contamination of a polypeptide by another point variation analog that was, at least in part, co-synthesized with the polypeptide of the major peak. An exemplary set of such chromatograms is shown in FIG. 8. Although a nitrogen atmosphere was not maintained during the coupling steps, little oxidation of methionine or tryptophan residues was evident in either the HPLC or amino acid analyses. The polypropylene mesh packets remained unchanged during the procedures.

The final wash step prior to commencement of the synthesis effectively removed the small amount of fine resin particles. It was found that removal of resin fines could also be accomplished by using the synthesis means to contain the chloromethyl resin during the cesium salt procedure that was utilized to couple the first BOC-protected amino acid residue. Gisin, *Helv. Chem., Acta,* 56, 1476–1482 (1973).

2. ELISA Results

An indication of the extent of binding of the various analogs relative to the control polypeptides with antibodies produced by a single monoclonal cell line are represented in FIG. 6. FIG. 7 shows decreases in binding relative to the control polypeptide. As is seen from FIG. 6, there was no significant difference in the binding relative to the control sequence corresponding to residues 98-110 of HA1 for any amino acid variation at positions 98(Y), 99(P), 100(Y), 102(V), 103(P), 105(Y), 107(S), 108(L), 109(R), or 110(S).

A dramatic loss of binding ability relative to the control was observed (FIG. 7) for polypeptides in which the aspartic acid (D) at position 101 was replaced with any other amino acid. Significant binding remained with replacements of 101(D) by glutamic acid, histidine, and asparagine only.

Though it is not immediately obvious from FIG. 6, a small but significant loss of binding ability occurs when the aspartic acid at position 104, and the alanine at position 106 are replaced with other amino acids. This loss of binding is more readily apparent by examination of FIG. 7, which shows the percent of decreased binding relative to the control peptide. The data in FIGS. 6 and 7 are arranged in order of increasing hydrophobicity Browne et al., in: *High Performance Liquid Chromatography of Proteins and Peptides,* Hearn et al., eds., Academic Press, NY, 65-72 (1983). Within the limits of resolution, little correlation was found between the binding ability and the hydrophobicity of the individual amino acids.

3. Discussion

An examination of the interaction of monoclonal antisera generated from a polypeptide corresponding to residues 75-110 of the hemagglutinin molecule was desired at the single amino level. A number of monoclonal antisera had been generated against residues in the area of 90-110 of the original polypeptide 75-110 which also recognized the native hemogluttinin molecule. It was desired to know the exact residues responsible for the specific antigen/antibody interaction and also which residues could be replaced by other natural or D-amino acids while maintaining the antigen/antibody interaction.

In the results presented here a series of 20 different 13 residue polypeptides were desired for each position of residues of 98-110 of hemagglutinin; i.e., YDYDVPDYASLRS.

For this study a complete series of 248 [13×20=260−12 redundant sequences =248] different single point amino replacement sets, as well as the 13 single position D-amino acid replacement series and the 13 single position omission analogs were desired. This was a total of over 280 different polypeptides. This number of polypeptides would be prohibitive both in terms of time, cost, and effort using conventional methods.

Using previously known techniques, if one desired to examine the effects of varying the residue at position 108 (i.e., L,leu) from the amino-terminus with each of the other natural L-amino acids, none but the first two residues could be synthesized using automated methods in a single synthesis, with the remaining eleven residues of each of those polypeptides necessarily requiring individual syntheses. In other words, 20 analogs until now would very probably require 20 completely separate syntheses. If all the residues in the polypeptide except those at the varying position could be synthesized at the same time, a great deal of time and expense could be saved.

A method of this invention using small, solvent permeable synthesis means that contain the individual polypeptide resin particles, effectively isolated the individual, different polypeptide-linked particles from each other during synthesis. That isolation and prevention of intermingling of amino acid residue subunit-linked particles by enclosure of particles containing amino acid residues of different identities in containers of separate synthesis means permitted simultaneous synthesis of all of the nineteen non-redundant, related single replacement polypeptide sequences, except for the nineteen steps at which the single replacement residues were polypeptide-bonded to the sequences.

Thus, a usual synthetic procedure to prepare nineteen 13-residue polypolypeptides would require 247 separate couplings, plus deprotection and neutralization steps, for a total of 741 steps, excluding washes. On the other hand, use of synthesis means and a method of this invention required only 31 separate couplings, plus deprotection and neutralization steps, for a total of 93 steps, excluding washes.

The before-described results of the individual syntheses that showed usually observed purity by amino acid analysis, and an absence of substantial intermingling of synthesised sequences by the HPLC results, coupled with the tremendously decreased number of steps required to prepare nineteen single replacement sequences illustrate a benefit of this invention in that polypeptide sequences of comparable purity to these prepared by usual techniques could be prepared using about one-eighth the number of steps that would typically be required, excluding washes.

B. Materials and Methods

1. Synthesis of Peptides (a) General Methods

Polypropylene mesh (0.74 micron interstices, Spectrum Medical Industries, Inc.) containers were prepared, having approximate dimensions of 20 millimeters (mm)×25 mm, using a 4 mm track width heat sealer (TEW Electric Heating Equipment Co., Inc.). After sealing two parallel sides together, the bottom of the packet was sealed along a line drawn by a colored marking pen (Sanford black, red, and blue sold under the trademark "SHARPIES") used to color code a series of containers.

After washing the containers with the methylene chloride to remove excess ink, and drying and weighing each container, a known amount of standard 200-400 mesh BOC-amino acid-linked resin [0.1-1.0 milliequivalents per gram (meq/gm)] was added. Typically 50-100 mg of resin was used. The BOC-amino acid resin was prepared following usual procedures as described before, and utilized a commercially available chloromethyl styrene resin having a known amount of chloromethyl groups (reactive benzyl moieties), BOC-protected amino acids and cesium chloride. When a larger amount of peptide was desired containers with larger dimensions were easily made.

After placing an identifying number at the top of the unsealed bag with a black marking pen, the container was closed and the number was permanently sealed into the polypropylene by over-sealing twice to give an 8 mm wide readable code for each synthesis means so prepared. A final thorough washing of the resin-enclosed synthesis means to remove fines and excess marking ink was carried out and was followed by drying and a final weighing to provide the known amount of particles finally in synthesis means.

The synthesis means so prepared were used directly for multiple analog peptide syntheses (MAPS); i.e., syntheses in which many analogs of a particular peptide are produced simultaneously. The synthesis means are also useful for simultaneous multiple peptide syntheses (SMPS); i.e., syntheses in which many different peptides are produced simultaneously. The previously described envelopes are particularly useful for both SMPS and MAPS.

The specific deprotecting, neutralization, coupling, and wash protocols used in this study were variations of Merrifield's original solid phase procedures [Merrifield, J. Am. Chem. Soc., 85, 2149-2154 (1963)] and are described in detail elsewhere [Houghten et al., Inst. J. Pept. Prot. Res., 16, 311-320 (1980); Houghten et al., Eur. J. Biochem., 145, 157-162 (1984)]. Briefly, the alpha amino-protected BOC-amino acids were purchased from BACHEM, LA or Chemical Dynamics, Rahway N.J., and were recrystallized if necessary. All alpha amino-protected BOC-amino acids were pure by thin layer chromatography, optical rotation and melting point. The following side chain protecting groups were used: O-benzyl for aspartic acid, glutamic acid, serine, and threonine; N-(ortho-chlorobenzyloxycarbonyl) for lysine; O-(meta-bromobenzyloxycarbonyl) for tyrosine; $N^g$-tosyl for arginine; N-im-dinitrophenyl for histidine and para-methoxybenzyl for cysteine. Asparagine and glutamine were coupled in the presence of N-hydroxylbenztriazole [Hruby et al., Angew. Chem. Int. Ed. Engl. 10, 336-339 (1971)].

(b) Synthesis of single amino acid variation analogs.

Using a Vega model 250c, a Biosearch SAM-II peptide synthesizer, or completely manual methods forty to eighty individual synthesis means containing desired, starting polypeptide-linked resins were carried through their common BOC removal, wash, and neutralization steps. As many as 100 peptides can be synthesized simultaneously per machine using a SAM-II synthesizer.

Following the final methylene chloride washes, the synthesis means containing neutralized, free alpha amine reactive group peptide-linked particles were removed from the reaction vessel and added solutions of their point variant protected amino acid present as symmetrical anhydrides [Wieland et al., Angew. Chem. Int. Ed. Engl., 10, 336-339 (1971)]. The coupling steps were carried out for a period of 60 minutes with stirring at room temperature. After completion of the coupling steps the particle-linked reaction product-containing synthesis means were returned to the reaction vessel, and the synthesis was continued through additional cycles of common rinse, deprotection, neutralization, and coupling steps until the syntheses were completed.

Specific variations of analogous peptides such as, residue replacements or omissions, or chain lengthenings or shortenings were easily accomplished by removing individual, identified synthesis means at the point of variation during the synthesis, carrying out the desired variation separately and, if appropriate, returning the packet to the common reaction vessel for completion.

Following the synthesis of a series of peptides, the particle-enclosing containers were washed thoroughly, dried, and weighed to give an initial indication the extent of of coupling completion. The resulting protected peptide reaction products were then severed from the particles using conventional hydrogen fluoride/anisole procedures [Houghten et al., Int. J. Pep. Prot. Res., 16, 311-320 (1980)] in a vessel modified to allow cleavage of twenty synthesis means-containing peptide resins at once.

Following extraction of the residual anisole with ether or ethyl acetate, the severed peptide reaction products were separated from the resin particles by extraction with 5% acetic acid. The separated polypeptide reaction products were collected either by direct lyophilization, or by desalting by passage through a SEPHADEX G-10 (Pharmacia Fine Chemicals, Piscataway, N.J.) followed by lyophilization. The crude peptide reaction products so obtained were characterized by HPLC, and were found to have an average purity of 84% (65%-94%).

The HPLC system used consisted of two Beckman 110A pumps controlled by a Beckman 421 controller, a Bio-Rad As-48 automatic sample injector with a 20 microliter loop, an Alltech ODS-3 5 micron particle size 4.6 mm I.D.×25 centimeter column, a Hitachi 100-20 variable wavelength spectrophotometer set at 220 nm and a Shimadzu C-R3A chromatopac integrator/recorder. The mobile phase consisted of a linear gradient of 20% Acetonitrile/80% $H_2O$/0.1% trifluoroacetic acid (TFA) going to 80% Acetonitrile/20% $H_2O$/0.1% TFA in 20 minutes. The flow rate was 1.0 milliters per minute.

The amino acid compositions of the individual peptides were determined using an LKB mode 4150 amino acid analyzer following the hydrolysis of the individual peptide reaction products in constant boiling HCL for 24 hours at 110° C. Values from amino acid analyses were all between ±10% of theory.

2. Monoclonal Antisera

The preparation of the monoclonal antibodies used in this study was described in detail elswhere. See, Niman et al., Proc. Natl. Acad. Sci. USA, 80, 4949-4953 (1983); Wilson et al., Cell, 37, 767-778 (1984). Briefly, a peptide consisting of residues 75-110 of HA1 chain of the H3 subtype X:47-A/Victoria/3/75 [Min Jou, Cell, 19, 683-696 (1980)] was coupled to keyhole limpet homocyanin (KLH) and was used to immunize 129 GIX+ mice. Spleen cells from those mice were fused with SP2/0 myeloma cells with polyethylene glycol 1500 (Baker). The fused cells were resuspended in 400 ml of Dulbecco's high-glucose minimal essential medium containing 10% fetal calf serum, 100 micromolar (uM) hypoxanthine, 1.0 uM methotrexate, and 16 uM thymidine, and were plated and grown onto 30 microtiter plates as described by Niman and Elder, Proc. Natl. Acad. Sci. USA, 77, 4524-4528 (1980). The hybridoma denominated 20CO 1 was used [Wilson et al., Cell, 37, 767-778 (1984).

3. ELISA Methods and Materials

ELISAs for determination of the percentage of binding of the analogs relative to the control peptide were carried out with 10 nanomoles of each peptide adsorbed to separate wells of 96 well microtiter plates (Costar ½ area EIA plates). Peptides were adsorbed to microtiter plates by admixture and maintainence .(incubation) in pH 9.6 carbonate/bicarbonate buffer at room temperature for eight hours. The plates were then washed 10 times with de-ionized water to remove unbound peptide. Blocking to prevent non-specific adsorption of the anti-sera was accomplished by incubating the plates with 100 microliters (ul)/well of 1% bovine serum albumin in phosphate buffered saline (BSA/PBS) for 1 hour at 37° C.

Monoclonal antibodies were bound to the peptides at a 1:10 dilution of cell-free supernatant in 1% BSA/PBS using a volume of 25 ul/well, and were incubated at 37° C. for 1 hour. Following 10 washes with de-ionized water to remove unbound antibody, horseradish peroxidase-conjugated rabbit antimouse IgG (Zymed Laboratories, Burlingame, CA) was added to each well at a dilution of 1:3000 in 1% BSA/PBS, and was incubated for 1 hour at 37° C. Excess conjugate antibody was removed by washing as before with de-ionized water.

The amount of conjugated antibody bound in each well was quantitated by reaction for twenty minutes with an aliquot from a freshly prepared developing solution of 24 milligrams o-phenylenediamine (Pitman-Moore, Inc., Washington Crossing, N.J.) and 1.0 ml 3% hydrogen peroxide in 50 ml de-ionized water. The resulting color was read at 495 nanometers (nm) by a Titertek Multiscan spectrophotometer (Flow Laboratories, Melbourne, Australia). Representative binding curves were determined by varying the amount of antigen adsorbed to the plate through serial two-fold dilutions down a row of wells of peptide added to the top well of the plate, and completing the assay as described above.

The present invention has been described with respect to preferred embodiments. It will be clear to those skilled in the art that modifications and/or variations of the disclosed synthesis means, envelopes and methods can be made without departing from the scope of the invention set forth herein.

What is claimed:

1. A means for carrying out a sequential, solid phase organic synthesis to form a reaction product containing a plurality of reacted subunits comprising an immersible mesh packet having enclosed therein a free form aliquot of reactive particles, said particles being of a size that is larger than any of the foraminae defined by said mesh packet and having a known amount of organic synthesis reactive functionality covalently linked to said particles, said reactive functionality being capable of reacting during said organic synthesis, said mesh packet and said particles being substantially insoluble in water and in organic solvents.

2. The synthesis means according to claim 1 wherein said mesh packet comprises a material selected from the group consisting of polymerized ethylene and propylene monomers.

3. The synthesis means according to claim 2 wherein said mesh of said packet is polypropylene mesh.

4. The synthesis means according to claim 3 wherein said mesh of said packet is heat sealed to enclose said particles.

5. The synthesis means according to claim 1 wherein said reactive functionality of said particles is a benzyl moiety that is a portion of a polymerized resin.

6. The synthesis means according to claim 5 wherein said resin constitutes substantially all of each of said particles.

7. The synthesis means according to claim 6 wherein the resin of said particles is comprised primarily of polymerized styrene cross-linked with divinyl benzene and includes a known amount of polymerized vinyl benzyl moiety, said polymerized vinyl benzyl moiety constituting said reactive benzyl moiety and providing a functional group through which said subunits may be covalently linked to said particles.

8. The synthesis means according to claim 7 wherein said reactive benzyl moiety is selected from the group consisting of benzyl chloride and benzylamine.

9. The synthesis means according to claim 5 wherein said particles are non-reactive with hydrogen fluoride.

10. The synthesis means according to claim 1, including a plurality of said foraminous container means each having enclosed therein said known quantity of said reactive particles, said plurality of container means being integrally formed with each other.

11. A means for carrying out a solid phase organic synthesis to form a reaction product containing a plurality of reacted subunits comprising an immersible mesh packet having enclosed therein a free form aliquot of solid support particles, said particles being of a size that is larger than any of the foraminae defined by said container and being linked to a known amount of identical organic synthesis subunits by selectively severable covalent bonds, each of said subunits containing a functional group capable of reacting during said organic synthesis, but that is protected from so reacting by a selectively removable covalently linked protecting group, said packet and said particles being substantially insoluble in water and organic solvents and being non-reactive with hydrogen fluoride.

12. The synthesis means according to claim 11 wherein said mesh packet comprises a material selected from the group consisting of polymerized ethylene, propylene and mixtures thereof.

13. The synthesis means according to claim 12 wherein said mesh in said packet is made from polypropylene mesh.

14. The synthesis means according to claim 11 wherein said particles are hydrophobic resin beads.

15. The synthesis means according to claim 14 wherein the resin of said beads is comprised primarily of polymerized styrene cross-linked with divinyl benzene and includes a known amount of polymerized vinyl benzene moiety through which said subunits are covalently linked to said beads.

16. The synthesis means according to claim 15 wherein said subunits- are selected from the group consisting of (i) an alpha amino group-protected amino acid residue and (ii) an alpha amino group-protected and reactive side chain-protected amino acid residue.

17. The synthesis means according to claim 16 wherein said alpha amino group protecting group is an N-tert-butoxycarboxyl group.

18. The synthesis means according to claim 17 wherein said amino acid residue is linked to said resin through an ester bond between the carboxyl group of said amino acid and said polymerized vinyl benzyl moiety.

19. The synthesis means according to claim 17 wherein said amino acid residue is linked to said resin through an amide bond between the carboxyl group of said amino acid residue and the amino group of a disulfide-containing linking group that is bonded to said polymerized vinyl benzyl moiety, said linking group, written in the direction from left to right and from said amino acid toward said benzyl moiety, being represented by the formula:

$$-NHCH_2CH_2SSCH_2(CH_2)_xCONH-$$

wherein x is a numeral having the value of zero or one.

20. A method of carrying out an organic solid phase synthesis to form a reaction product containing a plurality of desired reacted subunits comprising the steps of:
(a) providing a solid phase organic synthesis means comprising an immersible mesh packet having enclosed therein a free form aliquot of reactive particles, said particles being of a size that is larger than any of the foraminae defined by the mesh packet and having a known amount of organic synthesis reactive functionality covalently linked to said particles, said reactive functionality being capable of reacting during said organic synthesis, said packet and said particles being substantially insoluble in water and organic solvents;

(b) immersing said mesh packet in a liquid reaction medium containing first subunits and reacting the first subunits with said reactive functionalities to form within the immersed packet a selectively severable covalent bond between said first subunits and said particles, and to form a synthesis means containing particle-linked subunits, said first subunits including a first functional group that reacts with said reactive functionality and a second reactive functional group capable of reacting during said reaction, but that is protected from reaction by a selectively removable, covalently linked protection group;

(c) removing said protecting group from said second reactive functional group while said packet is immersed in a liquid medium to form a synthesis means containing particle-linked subunits having free reactive functional groups;

(d) admixing with the synthesis means containing particle-linked subunits having free reactive functional groups, while said packet is immersed in a liquid medium, an excess of identical, known other subunits that contain (i) a functional group capable of reacting with the free reactive groups of said particle-linked subunits and (ii) a second reactive functional group capable of reacting during the organic synthesis, but that is protected from so reacting by a selectively removable covalently linked protecting group;

(e) reacting said free reactive groups and said admixed functional groups, while said packet is immersed in a liquid medium, to form covalent bonds, couple the subunit to the particle and form particle-linked subunit reaction products;

(f) separating unreacted subunits from said particle-linked reaction products;

(g) removing the protecting groups of the coupled subunits of step (d), while said packet is immersed in a liquid medium, to form particle-linked reaction products containing free reactive functional groups;

(h) thereafter, serially repeating steps (d), (e), (f) and (g) until particle-linked reaction products containing the desired numer and identity of reacted subunits are synthesized;

(i) severing said selectively severable bond between said first subunit and said particle to form a mixture of severed, free reaction products and reacted particles;

(j) separating said severed, free reaction products from said reacted particles; and (k) recovering said severed reaction products.

21. The method according to claim 20 wherein said particles are hydrophobic resin beads.

22. The method according to claim 21 wherein the resin of said beads is comprised primarily of polymerized styrene cross-linked with divinyl benzene and includes a known amount of polymerized vinyl benzene moiety through which said subunits are covalently linked to said beads.

23. The method according to claim 22 wherein said subunits are selected from the group consisting of (i) an alpha amino group-protected amino acid residue and (ii) an alpha amino group-protected and reactive side chain-protected amino acid residue.

24. A method of carrying out an organic solid phase synthesis to form a reaction product containing a plurality of desired reacted subunits comprising the steps of:

(a) providing a solid phase organic synthesis means comprising an immersible mesh packet having enclosed therein a known quantity of resin particles having a known amount of a selectively severable, covalently linked identical organic synthesis subunits that include a selectively removable protecting group covalently bonded to a reactive functional group, said resin particles being of a size that is larger than any of the foraminae defined by said mesh packet, said packet and said particles being substantially insoluble in water and organic solvents and non-reactive with hydrofluoric acid;

(b) immersing said mesh packet in a liquid reaction medium for removal of said protecting group and selectively removing said protecting group to form within the immersed packet a synthesis means containing resin-linked subunits having a free reactive group;

(c) admixing, while said packet is immersed in a liquid medium, an excess of identical subunits that contain (i) a second reactive functional group capable of reacting with the free reactive groups of said resin-linked subunits, and (ii) another reactive functional group that is capable of reacting during said organic synthesis, but that is protected from so reacting by a selectively removable, covalently bonded protecting group;

(d) reacting said free reactive groups and said second reactive groups, while said packet is immersed in a liquid medium, to form covalent bonds, couple said admixed subunit to the resin and form resin-linked reaction products;

(e) separating unreacted subunits from said resin-linked reaction products;

(f) selectively removing the protecting groups said coupled subunits of step (c), while said packet is immersed in a liquid medium, to form resin-linked reaction products containing free reactive functional groups;

(g) thereafter, serially repeating steps (c), (d), (e) and (f) until resin-linked reaction products containing the desired number of reacted subunits are synthesized;

(h) severing said selectively severable bond between said first-named subunits and said resin to form free reaction products and reacted particles;

(i) separating said free reaction products from said reacted particles; and (j) recovering said severed reaction products.

25. The method according to claim 24 wherein the resin of said particles is comprised primarily of polymerized styrene cross-linked with divinyl benzene and includes a known amount of polymerized vinyl benzyl moiety through which said subunits are covalently linked to said particles.

26. The method according to claim 25 wherein said subunits that contain a selectively removable protected reactive functional group are N-tert-butoxycarbonyl-protected amino acid residues.

27. The method according to claim 26 wherein said amino acid residue is linked to said resin through an ester bond between the carboxyl group of said amino acid and said polyerized vinyl benzyl moiety.

28. The method according to claim 25 wherein said amino acid residue is linked to said resin through an amide bond between the carboxyl group of said amino acid and the amino group of a disulfide-containing linking group that is bonded to said polymerized vinyl benzyl moiety, said linking group, written in the direction from left to right and from said amino acid toward said benzyl moiety, being represented by the formula:

—NHCH$_2$CH$_2$SSCH$_2$(CH$_2$)$_x$CONH— wherein x is a numeral having the value of zero or one.

29. A method for simultaneously adding a subunit to each of a pluraltiy of resin particle-linked subunits in an organic solid phase synthesis comprising the steps of:
  (a) providing a pluraltiy of synthesis means each of which comprises an immersible mesh packet having enclosed therein a known quantity of particles, said particles being of a size that is larger than any of the foraminae defined by said mesh packet and having a known amount of an organic synthesis subunit covalently linked to said particles by selectively severable bonds, the subunit distal to the particle/subunit link containing a reaction functional group capable of reacting during said organic synthesis, but that is protected from so reacting by a selectively removable covalently bonded protecting group, said packet and said particles being substantially insoluble in water and organic solvents;
  (b) immersing each said mesh packet in a liquid reaction medium for removal of said protecting group and selectively removing said protecting group from said particle-linked subunits in each of said synthesis means to form an admixture containing a plurality of synthesis means containing particle-linked subunits having free reactive groups;
  (c) immersing said synthesis means in a liquid medium containing an excess of identical subunits each of which contains (i) a second reactive functional group capable of reacting with the free reactive group of another reactive functional group that is capable of reacting said particle-linked subunits and (ii) another reactive functional group that is capable of reacting during said organic synthesis, but that is protected from so reacting by a selectively removable, covalently bonded protecting group;
  (d) froming covalent bonds between said free reactive groups and said second reactive group, while said packet is immersed, to couple said admixed subunits to said particles and form a plurality of synthesis means that contain particle-linked reaction products whose distal subunits contain selectively removable, protected reactive functional groups;
  (e) separating said admixed, unreacted subunits from said particle-linked reaction products; and
  (f) thereafter separating said plurality of synthesis means from each other.

30. The method according to claim 29 wherein said particles include a resin and said subunits are linked to said particles through said resin.

31. The method according to claim 30 wherein the resin of said particles is comprised primarily of polymerized styrene cross-linked with divinyl benzene and includes a known amount of polymerized vinyl benzyl moiety through which said subunits are covalently linked to said particle.

32. The method according to claim 31 wherein said subunits that contain a removably protected reactive functional group are N-tert-butoxycarbonyl-protected amino acid residues.

33. The method according to claim 32 wherein said amino acid residue is linked to said resin through an ester bond between the carboxyl group of said amino acid and said polymerized vinyl benzyl moiety.

34. The method according to claim 31 wherein said amino acid residue is linked to said resin through an amide bond between the carboxyl group of said amino acid and the amino group of a disulfide-containing linking group that is bonded to said polymerized vinyl benzyl moiety, said linking group, written in the direction from left to right and from said amino acid toward said benzyl moiety, being represented by the formula:

—NHCH$_2$CH$_2$SSCH$_2$(CH$_2$)$_x$CONH— wherein x is a numeral having the value of zero or one.

35. The method according to claim 29 wherein said linked subunits are amino acid residues polypeptide bonded in a reaction product sequence.

36. The method according to claim 35 wherein said amino acid residue reaction product sequences correspond to the amino acid sequence of a single proteinaceous material except for the identify of one amino acid residue in each of said subunit reaction product sequences.

37. The method according to claim 29 further including serially repeating strps (c), (d) and (e) prior to step (f) until plural synthesis means are produced in which each of said synthesis means contains a particle-linked subunit reaction product having a desired number and identity of reacted subunits.

38. The method according to claim 29 further including the steps of
  (g) immersing said separated synthesis means in a liquid reaction medium for removal of said distal protecting group and selectively removing the distal protecting group from the subunit reaction products of at least one of the separated the subunit reaction products of at least one of the separated synthesis means of step (f) to form a synthesis means containing particle-linked subunits having free reactive groups;
  (h) immersing said synthesis means formed in step (g) in a liquid medium containing an excess of identical subunits each of which contains (i) a second reactive functional group capable of reacting with said free reactive groups of the particle-linked subunits, and (ii) another reactive functional group that is capable of reacting during said organic synthesis, but that is protected from so reacting by a selectively removable, covalently bonded protecting group;
  (i) forming covalent bonds between said free reactive groups and said second reactive group, while the synthesis in step (g) is immersed in a liquid medium to couple said admixed subunits to said particles and form a synthesis means containing particle-linked reaction products whose distal subunits contain selectively removable, protected reactive functional groups;

(j) separating unreacted subunits from the particle-linked reaction products contained in synthesis means produced in step (i);

(k) therqafter combining said synthesis means produced in step (i) with another synthesis means to form a new plurality of synthesis means, each comprising an immersible mesh packet having enclosed therein a known quantity of particles, said particles being of a size that is larger than any of the foraminae defined by said mesh packet and having a known amount of organic synthesis subunit covalently linked to said particles by selectively severable bonds, the subunit distal to the particle/subunit link containing a reactive functional group capable of reacting during said organic synthesis, but that is protected from so reacting by a selectively removable, covalently bonded protecting group, said packet and said particles being substantially insoluble in water and organic solvents;

(l) selectively removing said distal protecting groups from said particle-linked subunits in each of said new plurality of synthesis means to form a further plurality of synthesis means containing particle-linked subunits having free reactive groups;

(m) immersing said further pluraltiy of synthesis means in a liquid medium containing an excess of identical subunits each of which contains (i) a second functional group capable of reacting with the free reactive functional group of said particle-linked subunits, and (ii) another reactive functional group that is capable of reacting during said organic synthesis, but that is protected from so reacting by a selectively removable, covalently linked protecting group;

(n) forming covalent bonds between said free reactive groups and said second reactive groups, while said further plurality of synthesis means is immersed in a liquid medium to couple said admixed subunits to said particles and form an additional plurality of synthesis means that contain particle-linked reaction prodcuts whose distal subunits contain selectively removable, protected reactive functional groups;

(o) separating said admixed, unreacted subunits from said particle-linked reaction products; and (p) thereafter separating individual synthesis means constituting said additional pluraltiy of synthesis means from each other.

39. The method according to claim 38 wherein individual synthesis means of the new pluraltiy of synthesis means contain different subunits.

40. The method according to claim 29 wherein a portion of the synthesis means constituting the plurality of synthesis means in step (a) is enclosed in a resealingly closable, foraminous envelope means, said envelope means comprising first and second opposing webs at least one of which is foraminous, said webs being partially secured together at their peripheries; said first web being operably connected to a male portion of a resealable clsoure means, and said second web being operably connected to a female defines a mouth which communicates with the interior of said envelope means, said male and female portions of said closure means matingly engaging to resealably close said envelope means when pressed together in face-to-face relation, the foraminae of said envelope means being sized to permit drainage of a solvent used in said synthesis within a time period of at least 5 minutes at synthesis temperature while retaining said synthesis means within said envelope means, said envelope means being substantially insoluble in water and organic solvents.

* * * * *

UNITED STATES PATENT AND TRADEMARK OFFICE
CERTIFICATE OF CORRECTION

PATENT NO. : 4,631,211

DATED : December 23, 1986

INVENTOR(S) : RICHARD A. HOUGHTEN

It is certified that error appears in the above-identified patent and that said Letters Patent is hereby corrected as shown below:

Col. 32, lines 48-49, delete "the subunit reaction products of at least one of the separated."

Col. 34, line 27, after "female" insert -- portion of said closure means whereby said closure means --.

Signed and Sealed this

Twenty-eighth Day of June, 1988

Attest:

DONALD J. QUIGG

Attesting Officer

Commissioner of Patents and Trademarks